(12) United States Patent
Matusch

(10) Patent No.: US 8,641,668 B2
(45) Date of Patent: Feb. 4, 2014

(54) DISPOSABLE INJECTOR WITH AT LEAST ONE TENSION HOOK

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 137 days.

(21) Appl. No.: 12/653,433

(22) Filed: Dec. 14, 2009

(65) Prior Publication Data

US 2010/0100040 A1 Apr. 22, 2010

Related U.S. Application Data

(63) Continuation-in-part of application No. PCT/EP2008/004947, filed on Jun. 19, 2008.

(30) Foreign Application Priority Data

Jul. 10, 2007 (DE) .......................... 10 2007 032 464

(51) Int. Cl.
*A61M 5/20* (2006.01)
*A61M 5/30* (2006.01)
*A61M 37/00* (2006.01)

(52) U.S. Cl.
USPC .............................. 604/134; 604/68; 604/131

(58) Field of Classification Search
USPC ............. 604/110, 131–137, 156–157, 68–72, 604/218
See application file for complete search history.

(56) References Cited

U.S. PATENT DOCUMENTS

| 3,557,784 | A | * | 1/1971 | Shields | ........................... 604/68 |
| 4,227,528 | A | | 10/1980 | Wardlaw | |
| 4,378,015 | A | | 3/1983 | Wardlaw | |
| 4,968,302 | A | | 11/1990 | Schluter et al. | |
| 5,681,291 | A | | 10/1997 | Galli | |
| 6,258,068 | B1 | | 7/2001 | Kirchhofer et al. | |
| 6,783,509 | B1 | * | 8/2004 | Landau et al. | .................. 604/70 |
| 2005/0020984 | A1 | | 1/2005 | Lesch, Jr. | |
| 2006/0129089 | A1 | | 6/2006 | Stamp | |
| 2008/0146997 | A1 | | 6/2008 | Hoffmann | |

FOREIGN PATENT DOCUMENTS

WO  WO 2006/088513 A1  8/2006

* cited by examiner

*Primary Examiner* — Nicholas Lucchesi
*Assistant Examiner* — Weng Lee
(74) *Attorney, Agent, or Firm* — R. S. Lombard; K. Bach

(57) ABSTRACT

A disposable injector with a housing (10) in which are arranged at least one mechanical spring energy reservoir (50), at least one cylinder/piston unit (100), at least one piston-actuating ram, and at least one trigger unit. For this purpose, the housing has at least one inverted draw hook, which has at least one support surface respectively in the region of its free end. The spring-loaded piston-actuating plunger rests on the support surface, whereby the contact zone placed between the draw hook and the piston-actuating plunger represents a variable-speed gear pair thrusting the draw hook radially outwards. The locking position of the draw hook is secured by an actuating element positioned in a locked position. The actuating element has a triggering position which effects radially outwards aligned retreat of the draw hook when the piston-actuating plunger is released.

12 Claims, 3 Drawing Sheets

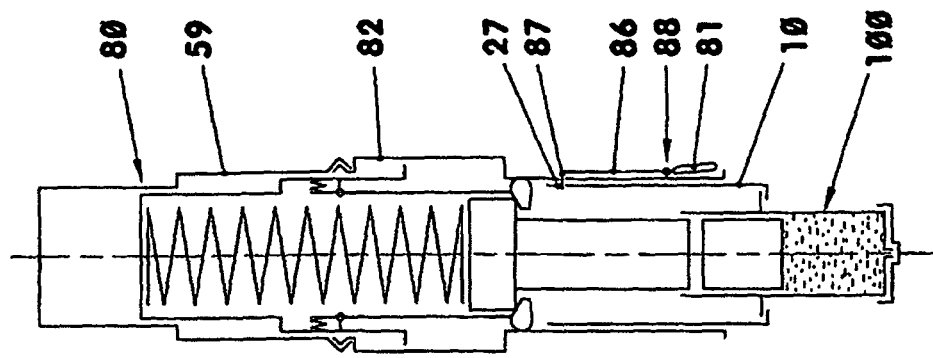
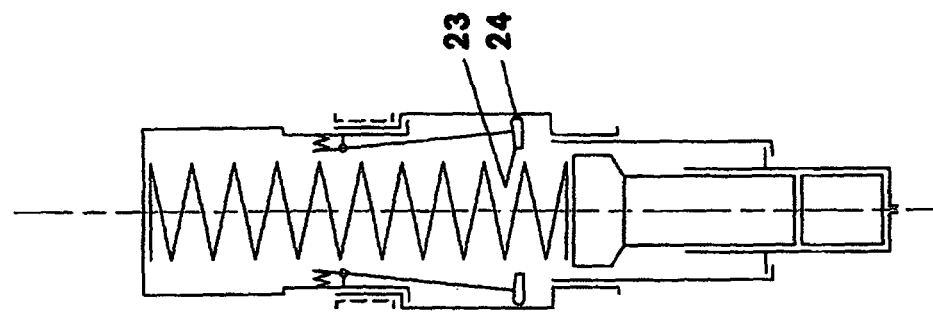
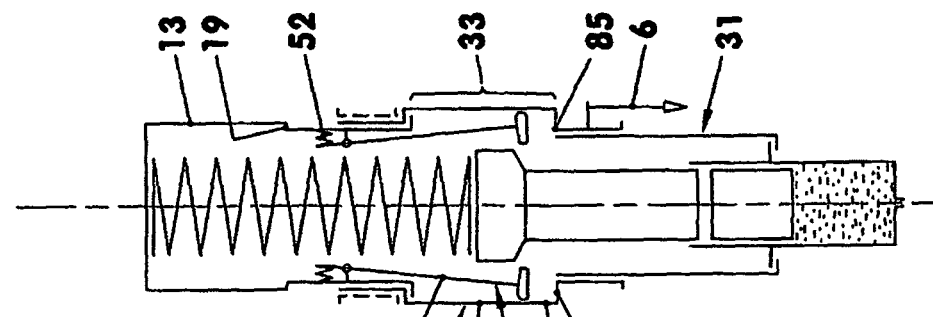
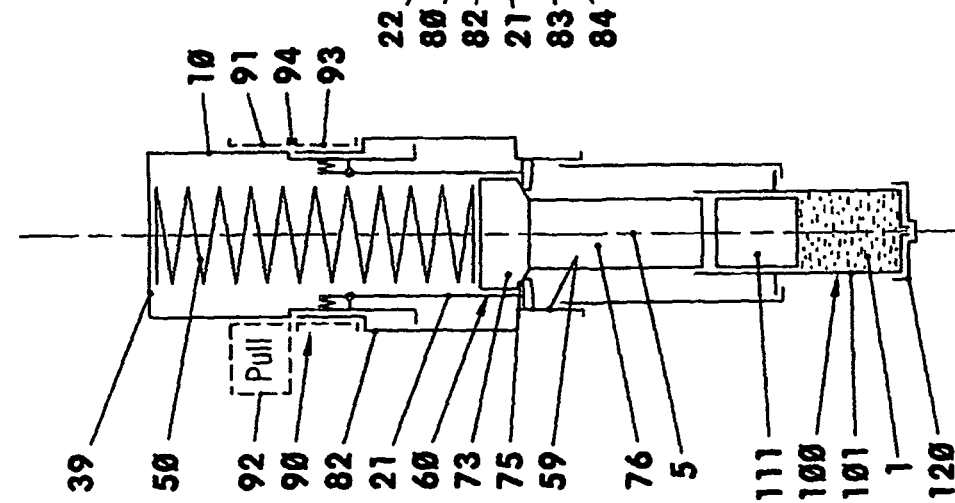

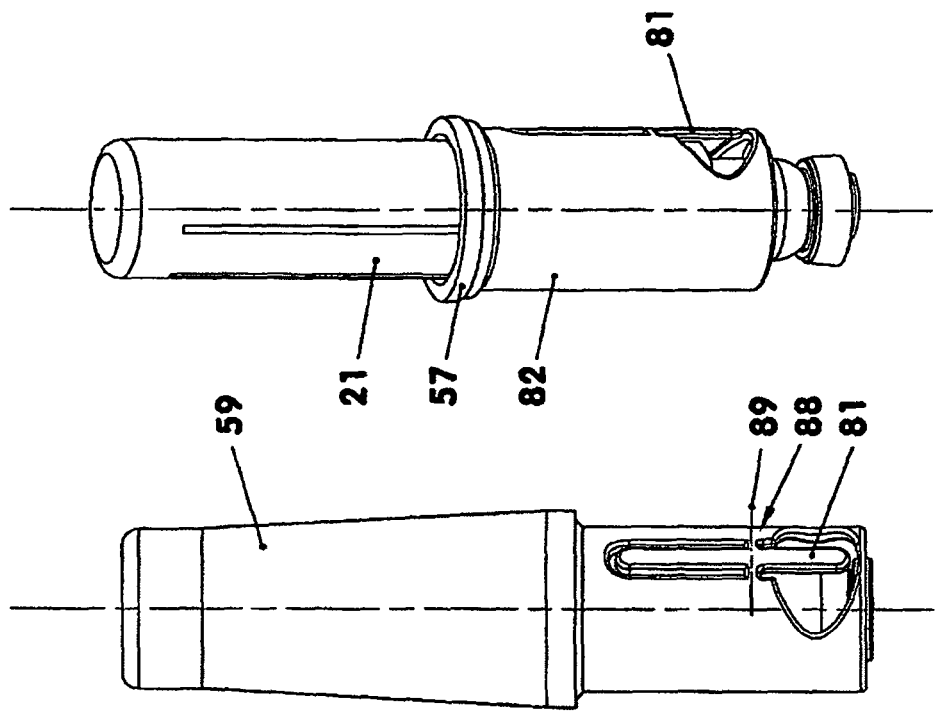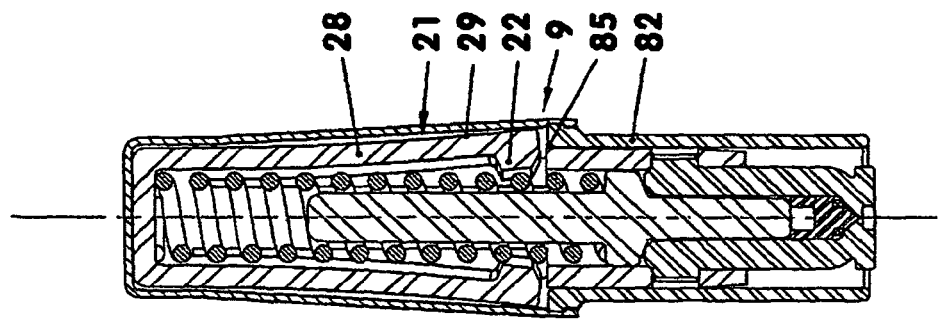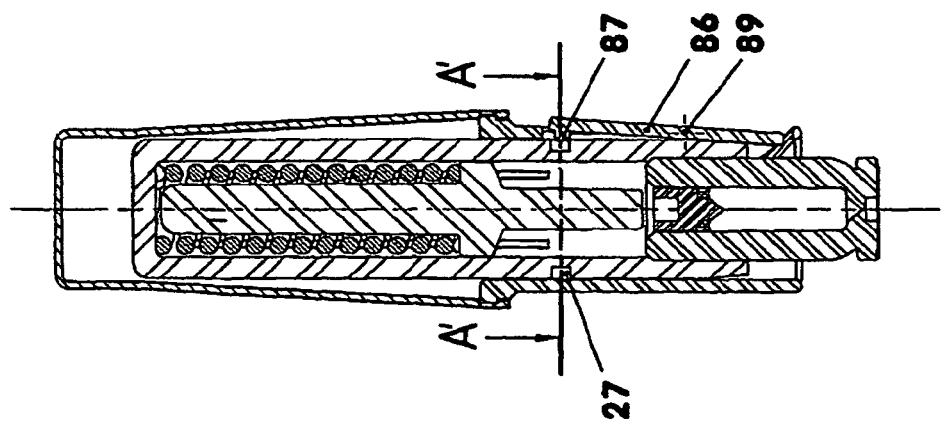

US 8,641,668 B2

DISPOSABLE INJECTOR WITH AT LEAST ONE TENSION HOOK

CROSS-REFERENCE TO RELATED APPLICATION

This is a continuation-in-part application of pending international application PCT/EP2008/004947 filed Jun. 19, 2008 and claiming the priority of German Application No. 10 2007 032 464.4 filed Jul. 10, 2007.

BACKGROUND OF THE INVENTION

The invention relates to a disposable injector with a housing, in which or on which—respectively at least in certain areas—at least one mechanical spring-energy storage, at least one cylinder-piston unit which can be filled at least occasionally with active ingredient, at least one piston-actuating plunger and at least one actuating unit are arranged, whereby the spring-energy storage includes at least one pre-stressed spring-loaded element and whereby at least part of the piston-actuating plunger is positioned between the spring-energy storage and the piston of the cylinder-piston unit.

DE 36 44 984 A1 discloses inter alia such an injector which has a spring-loaded, pre-stressed piston-actuating plunger, whereof the rearward plunger rod has elastic draw hooks at its free end. The draw hooks hold the piston-actuating plunger positively firmly on one edge of the injector housing. For this they have only minimal bearing surface on the housing. To activate the injector the draw hooks are pushed away from the edge holding them. As a result, the spring-loaded, pre-stressed piston-actuating plunger advances to complete injection.

The object of the present invention is therefore to develop a modular disposable injector which has only a few components for its minimal structural size and guarantees secure mounting and function with easy handling.

SUMMARY OF THE INVENTION

The present invention provides a disposable injector with a housing (10) in which are arranged at least one mechanical spring energy reservoir (50), at least one cylinder/piston unit (100), at least one piston-actuating ram (60), and at least one actuating trigger unit (80). For this purpose, the housing has at least one inverted draw hook (21), which has at least one support surface respectively in the region of its free end. The spring-loaded piston-actuating plunger rests on the support surface, whereby the contact zone placed between the draw hook and the piston-actuating plunger represents a variable-speed gear pair thrusting the draw hook radially outwards. The locking position of the draw hook is secured by an actuating element positioned in a locked position. The actuating element has a triggering position which effects radially outwards aligned retreat of the draw hook when the piston-actuating plunger is released.

The invention presents here for example a needle-free disposable injector, whereof the piston-actuating plunger is released with a triggering procedure of the disposable injector. For this purpose, for pre-stressing and holding the spring-energy storage the piston-actuating plunger is held positively and non-positively by at least one inverted draw hook arranged on the housing or integrated in the housing. The draw hook or the draw hooks are held by an actuating element until the disposable injector is used in its locked position. To trigger the injector the draw hook or the draw hooks are released by displacing the actuating element so that the piston-actuating plunger can move under the effect of the spring-energy storage at least approximately parallel to the centre line of the disposable injector.

BRIEF DESCRIPTION OF THE DRAWINGS

Further details of the invention will emerge from the following schematically illustrated embodiments, in which:

FIG. 1 illustrates a disposable injector with two draw hooks and label retainer;

FIG. 2 as for FIG. 1, however unlocked and actuated (fictitious state);

FIG. 3 as for FIG. 2, however following drug ejection;

FIG. 4 illustrates a disposable injector with two draw hooks and release lever retainer;

FIG. 8 as for FIG. 5, though unlocked;

FIG. 9 as for FIG. 5, however following drug ejection;

FIG. 10 illustrates a lateral elevation to FIG. 9, but pivoted through 45° to the side;

FIG. 11 is a diametrical view of FIG. 8 without actuating cap.

DETAILED DESCRIPTION OF THE PARTICULAR EMBODIMENTS

Figure 6:
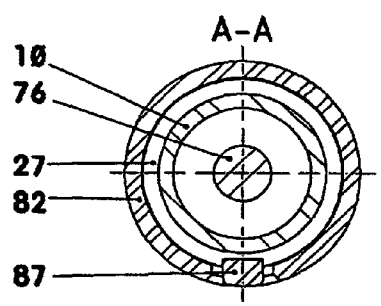
FIG. 6 shows cross-section A-A as in FIG. 5, or respectively A'-A' as in FIG. 8.

FIGS. 1 to 3 show a simplified principle of a disposable injector with permanently loaded spring-energy storage. The disposable injector comprises a housing (10), a cylinder-piston unit (100) filled with e.g. an injection solution, a piston-actuating plunger (60) and a screw compression spring (50) as spring-energy storage. Also, an actuating element (82) and a retaining element (90) are arranged on the housing (10).

The housing (10) is a pot-shaped hollow body, open at the bottom and with an elevated floor (39). The housing (10) has e.g. two opposite window-like openings (33) in the middle region, the jacket region (31). Articulated in the region of the respectively upper edge of the individual opening (33) is in each case an inverted draw or tension hook (21). The inverted draw hooks (21) are supported by means of the spring-loaded elements (52) on the housing (10). The spring-loaded elements (52), e.g. small screw compression springs, lie above the lag-hinges and attempt to press the lower, free ends of the draw hooks radially outwards.

Both draw hooks (21) hold the piston-actuating plunger (60) on its plunger disc (73) in its pre-stressed position. For this purpose, the draw hooks (21) encompass with their support surfaces (23) and/or support edges the lower collar surface (75) of the plunger disc (73). The size of the respective contact surface between a support surface (23) and the corresponding front end (75) is in the region of 2 to 20 mm².

In FIGS. 1 to 3 the collar surface (75) has the form of a frustoconical jacket, whereof the apex angle is ca. 100 to 130 degrees, preferably 120 degrees of angle. The notional tip of the frustoconical jacket lies on the centre line (5) in the region of the piston slide (76). The draw hooks (21) lie on the collar surface (75) with narrow, almost continuous support surfaces (23). The contact surfaces behave inversely in FIG. 4, where the draw hooks (21) have large-surface support surfaces (23), which are in each case part of a frustoconical jacket. The plunger disc (73) lies with its for example rounded outer edge on these support surfaces (23).

Figure 5:
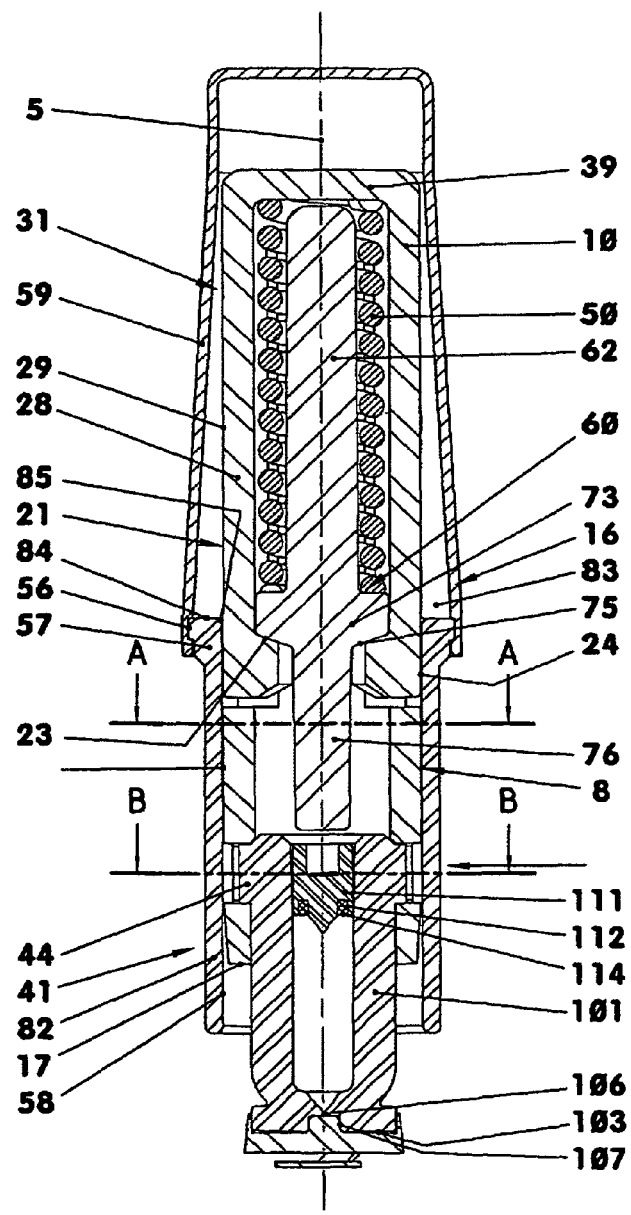
FIG. 5 illustrates a disposable injector with two draw hooks deformed in locked position.

A third kind of contact surface configuration would be fitting together large-surface contact surfaces, as in FIG. 5, where the collar surface (75) and the support surface (23) touch over their entire surface.

On the side averted from the centre line (5) each draw hook (21) has, for example, a curved, contact surface (24).

Located in the lower region of the housing (10) are holders for fastening the cylinder-piston unit.

In the embodiment the cylinder-piston unit (100) comprises a cylinder (101) filled with an injection solution (1), in which a piston (111) sits in the rear position. Above the piston (111) in the housing (10) the piston-actuating plunger (60) is e.g. arranged such that although it does not touch the piston, it is guided sideways by its lower end in the upper region of the cylinder (101).

According to FIG. 1 the housing (10) is enclosed in its middle region by the sleeve-like actuating element (82) covering e.g. the openings (33). The actuating element (82) is mounted to move lengthways on the radial outer surface (13) of the housing (10). It has a circumferential widened region (83) in the middle region. There can also be partially widened regions or uncovered openings instead of this widened region (83) in the case of a non-rotating symmetrical actuating element (82) per draw hook (21).

With respect to the housing (10) the widened region (83) is positioned and dimensioned so precisely that it can take up the outwards thrust draw hooks (21) which retreat during the triggering procedure. The inner contour of the widened region (83) is e.g. a channel with a return flank (84), which here represents a plane normal to the centre line (5) of the injector. The transition between for example the cylindrical inner wall of the actuating element (82) and the return flank (84) is configured e.g. as a sharp edge (85).

The screw compression spring (50) sits pre-stressed between the plunger disc (73) and the superjacent floor (39) of the housing (10). The resilient force is transferred via the plunger disc (73) to the draw hooks (21). Due to the inclination of the collar surface (75) and/or the inclination of the support surfaces (23), the draw hooks (21) are thrust radially outwards in the manner of a variable-speed gear. The release sleeve (82) steadily supports this radial force.

The piston-actuating plunger (60) arranged in the housing (10) is here divided into two regions. The lower region is the piston slide (76). Its diameter is slightly smaller than the inner diameter of the cylinder (101) of the cylinder-piston unit (100). The lower front end of the piston slide (76) acts directly on the piston (111).

The upper region, the plunger disc (73), is a flat disc, cylindrical at least in certain areas, whereof the outer diameter is a few tenths of a millimeter smaller than the inner diameter of the housing (10) in the jacket region (31).

The piston slide (76) can of course also be designed as a separate component, separate from the plunger disc (73). For this purpose it is placed on the inner wall of the housing (10).

The screw compression spring (50) sits pre-stressed between the plunger disc (73) and the elevated floor (39) of the housing (10).

According to FIG. 1 the actuating element (82) rests at the rear on a housing collar (19). Adhered to the rear section of the actuating element (82) and the housing region lying above the housing collar (19) is an adhesive label or banderole (90) divided into at least two regions as a securing element. The upper region is a tear-off strip (91), from which a tear-off tab (92) protrudes. The lower region is a retainer strip (93). The tear-off strip (91) and the retainer strip (93) have a straight perforation (94) or a continuous thin material site as their future separating line. The perforation (94) lies directly above the assembly joint laid between housing (10) and actuating element (82). To release the injector the tear-off strip (91) is peeled off the housing (10) by means of the tear-off tab (92). At this point the tear-off strip (91) tears off at the perforation (94) along the retainer strip (93). The connection between the housing (10) and the actuating element (82) is accordingly broken.

An adhesive label with inserted tear-off thread can also be used instead of the adhesive label with flat tear-off tab. The tear-off thread lies above the assembly joint. A plastic strip or a thin wire can also be used as a tear-off thread protruding at the end by a few millimeters. The adhesive label is separated into two parts in the vicinity of the assembly joint by tearing off the tear-off thread.

After the protective cap (120) is removed, the tear-off strip (91) is first pulled off to the side to detach the actuating element (82) from the housing (10) to activate the disposable injector. Then the actuating element (82) is enclosed by the hand formed into a fist and the disposable injector is positioned at the injection site and pressed against it. With this procedure the actuating element (82) slides forwards on the outer walls (13) of the housing (10), therefore towards the injection site. The contact surfaces (24) of the draw hooks (21) slip over the edge (85), as in FIG. 2. The draw hook end deviates into the widened region (83) and in the process releases the plunger disc (73). Now the piston-actuating plunger (60) can shoot down unhindered, as in FIG. 3. The cylinder (101) is emptied.

The actuating element (82) can of course also be gripped like a writing instrument to press it against the injection site for activation.

FIG. 4 shows an injector with an actuating unit (80), which encloses the housing (10) for the most part. For this purpose, an actuating cap (59), which fully encloses the rear or upper housing region, is attached to the sleeve-like actuating element (82).

Furthermore, a securing release lever (86) is attached or formed on the actuating element (82), instead of the adhesive label (90). At its lower end the release lever (86) has a compressible actuating element (81), at its upper end a latching tab (87) and between the parts (81) and (87) a lag-hinge (88) mounting the release lever (86). The latching tab (87) projects into and locks in a recess (27) of the housing (10), as in FIG. 4.

When the actuating element (81) is pressed the latching tab (87) of the release lever (86) pivots out of the housing recess (27). The securing latching between the housing (10) and the sleeve-like actuating element (82) is overridden. Now the actuating element (82) can be pushed in the direction of the cylinder-piston unit (100).

FIGS. 5 to 11 show an embodiment of the principle described in FIG. 4 and partially in FIGS. 1 to 3. Here also the load-bearing component is a one-piece housing (10). It is made from e.g. a fibreglass-reinforced polyamide by injection moulding. The housing (10) has an extensively tubular shape and is divided into two functional areas, comprising both the upper jacket region (31) and the lower fixing region (41).

The substantially tubular jacket region (31) is sealed at the top by an e.g. level floor (39). Located in the lower half of the jacket region (31) are two opposite formed-on draw hooks (21). The forming-on site for the draw hooks (21) is just under the floor (39). For forming the respective draw hook (21) there is located in the jacket region (31) a narrow, at least approximately U-shaped gap, surrounding the individual draw hook to the sides and at the bottom. Over ca. 80% of its length the draw hook (21) has the wall thickness and curve of the walls of the housing (10). This region inter alia also functions as a sprung-elastic flexional beam (28) and has a sickle-shaped cross-section.

If required, part of this flexional beam (28) can also be equipped with a rectangular cross-section to reduce bending stresses occurring from use in the flexional beam edge region. In FIG. 9 the draw hook (21) is shown in the undeformed state.

The lower free end of the individual draw hook (21) is here formed by the radially inwardly projecting hook element (22). The individual hook element (22) projects ca. 1.5 to 3 millimeters over the inner walls of the housing (10) and has at least one support surface (23) and one contact surface (24). According to FIG. 5 the plunger disc (73) of the stressed disposable injector lies on the support surface (23) by its collar surface (75). The support surface (23), here fulfilling the function of a wedge surface, has the form of a frustoconical jacket with an apex angle of 120 degree of angle.

At least in the contact region the draw hooks (21) or the collar surface (75) may have ceramic armouring. It is also possible to reinforce the collar surface (75) by an e.g. stuck-on, frustoconical surface-shaped washer similar to a cup spring.

The contact surfaces (24) of the hook elements (22) of the deformed draw hooks (21), as in FIG. 5, correspond here to the draw hook rear surface (29) and is at least approximately comparable to part of the outer walls (13). When the disposable injector is stressed the contact surface (24) contacts the inner walls (58) of the sleeve-like actuating element (82). If required, to minimize the surface pressure the contact surface (24) may have a curve, which corresponds to the inner walls (58).

According to FIG. 5 the housing (10) has ca. in the middle, as per intersection line A-A, an annular-channel-like recess (27), in which the latching tab (87) of the release lever (86) engages. FIG. 6 shows the engagement in cross-section. In this cross-section the actuating element (82) and the piston slide (76) are also evident.

Situated under the jacket region (31) is the fixing region (41) for taking up the incorporable cylinder-piston unit (100). The fixing region (41) is part of a bayonet socket. Arranged for this purpose on its inner walls are two or more angular channels (42), as in FIG. 7. The channels (42) lead upwards from the vertical from the lower housing front side (17) and merge respectively into a short horizontal channel section after a few millimeters. Here the horizontal channel section has a radially continuous recess above the vertical channel section.

Figure 7:
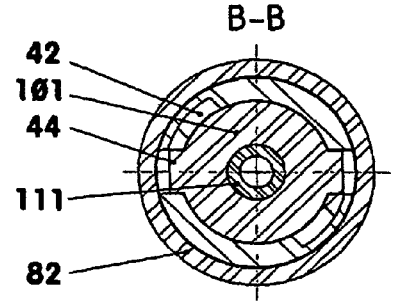
FIG. 7 shows cross-section B-B as in FIG. 5.

In the fixing region (41) the cylinder (101) is inserted and fixed via e.g. two or more bayonet catches (44), as in FIG. 7. One or more latching elements, which prevent the bayonet socket from being released, and thus the cylinder (101) from being removed, are located where required in the horizontal channel section or on at least part of the bayonet catches (44).

The cylinder (101) is e.g. a thick-walled pot. In the for example cylindrical bore of the cylinder (101) sits the rod-less piston (111). On its at least approximately conical front end the piston (111) has an axial annular groove (112) for receiving a sealing ring (114) or a permanently elastic sealing mass. Set into the rear front end of the piston (111) where required is an e.g. cylindrical metal plate.

Located in the centre of the bore of the cylinder (101), whereof the cylindrical floor matches the contour of the front piston front side at least approximately, is a short cylindrical, nozzle-like bore (106). Its diameter is ca. 0.1 to 0.5 millimeters. This bore (106) is one to five times as long as its diameter. It ends in a cylindrical recess (107) of the floor-side outer front end (103) of the cylinder (101).

In the fixing region (41) the outer walls of the housing (10) are designed frustoconical-surface shaped. The wall thickness tapers to the front side (17) by ca. 20%, so that the actuating element (81) can recede during actuation.

Arranged between the piston (111) and the floor (39) is the spring-energy storage (50) or respectively the drive unit of the disposable injector. The spring-energy storage (50) is a screw compression spring, arranged on the piston-actuating plunger (60) with the plunger disc (73). The resilience-stressed piston-actuating plunger (60) is supported on the draw hooks (21) of the housing (10) by means of the plunger disc (73).

Above the plunger disc (73) the piston-actuating plunger (60) has a pilot pin (62) which guides the screw compression spring (50). Located centrally under the plunger disc (73) in the extension of the pilot pin (62) is a piston slide (76), which acts on the piston (111) when the disposable injector is activated.

The actuating element (82) partially enclosing the housing (10) and the cylinder-piston unit (100) is here likewise a release sleeve, made of acrylonitrile butadiene styrene, known as ABS plastic for instance. The essentially cylindrical release sleeve (82) has at its upper end a flange-like, outwardly protruding collar (57). Attached to the collar (57) is an actuating cap (59), which fully encloses the rear end of the housing (10) with clearance, as in FIG. 10 also. The actuating cap (59) has at its lower end an annular groove (56), with which it sits firmly on the collar (57) of the actuating element (82).

This upper end of the actuating element (82) has the return flank (84) with the inner edge (85) as front end. Immediately above the return flank (84) in the actuating cap (59) is a cavity designated as widened region (83). Above the widened region (83), the actuating cap (59) in the vicinity of the floor (39) is capable of sliding on the outer walls (13) of the housing (10).

Integrated under the collar (57) in the at least approximately cylindrical region of the actuating element (82) is the release lever (86), as in FIGS. 8, 10 and 11. The latter is connected via a lag-hinge (88), e.g. a twistable material link, to the release sleeve (82). Together with the actuating element (81) the release lever (86) forms a rocker button, which has its pivot axis (89) in the vicinity of the lag-hinge (88), as in FIG. 10 also. If the release lever (86) is pressed against the housing (10) by pressure on the actuating element (81), at the other end of the release lever (86) the latching tab (87) releases the recess (27), as in FIG. 8. There is no illustration for the cutting path A'-A', however it corresponds to the cutting path A-A.

FIG. 8 shows the disposable injector with activated release lever, therefore released. In FIG. 9 the injector is shown with actuating element (82) pushed down.

When the release sleeve (82) is pushed down the flexional beams (28) with their rear surface (29) slip over the edge (85) outwards into the widened region (83), as in FIG. 9. The draw hooks (21) bend elastically outwards into their actual starting position. The draw hooks (21), now no longer deformed, release the piston-actuating plunger (60) so that the piston (111) is thrust abruptly into the cylinder (101) under the effect of the spring-loaded element (50). The injection procedure is completed with ejection of the drug by the cylinder-piston unit (100).

In this variant embodiment, with the exception of the spring-loaded element (50), all components can be arranged rotationally symmetrically and/or mirror-symmetrically to a plane laid on the centre line (5), which simplifies the assembly.

With injectors, in which the piston-actuating plunger (60) is guided straight in the housing (10)—at least in certain areas—with minimal clearance and the piston-actuating plunger (60) has adequate bending strength, only a single draw hook (21) can also be used instead of two or more draw hooks (21).

In the variants illustrated in the figures the individual contact zone between the draw hook (21) and the plunger disc (73) is designed as surfaces (23) and (75), which glide on each other on contact. In a particular configuration in each surface (23) of the individual draw hooks (21) a roller can be mounted, which rolls away as a roller bearing, therefore almost frictionless, when the injector is actuated on the surface (75) of the plunger disc.

With the exception of the spring-loaded element (50), where required a piston plate and for example the available bearing rollers of the draw hooks (21), all parts of the previously described disposable injectors are made of plastics or plastic- or rubber-like materials.

LEGEND 1 injection solution; drug
5 centre line of the disposable injector
6 actuation direction of movement of (82), downwards movement
8 locked position
9 triggering position
10 housing, one-piece
13 outer surface, cylindrical
16 release region, top
17 lower housing front side
19 housing collar
21 draw hook
22 hook elements
23 support surface, support edge
24 contact surface
27 recess, annular groove
28 flexional beam, flexural elastic element
29 rear surface
31 jacket region
33 openings
39 floor
41 fixing region for cylinder-piston unit
42 channels, angular
44 bayonet catches
50 spring-loaded element, screw compression spring, spring-energy storage
52 spring-loaded element of (21)
56 annular groove on (59)
57 collar on (82)
58 inner walls of (82)
59 actuating cap
60 piston-actuating plunger
62 pilot pin
73 plunger disc
75 collar surface, front end, bottom
76 piston slide
80 actuating unit
81 compressible actuating element
82 actuating element
83 widened region
84 return flank
85 edge, sharp-edged
86 release lever, securing element
87 latching tab
88 lag-hinge
89 pivot axis
90 adhesive label, securing element
91 tear-off strip
92 tear-off tab
93 retainer strip
94 predetermined breaking point, perforation
100 cylinder-piston unit
101 cylinder
103 front end
106 bore, nozzle
107 recess in front end
111 piston
112 annular groove
114 sealing ring, seal
120 sealing cap, adhesive seal

What is claimed is:

1. A disposable injector comprising:
a housing having at least one mechanical spring-energy storage connected thereto,
at least one cylinder-piston unit (100) which can be filled at least occasionally with active ingredient,
at least one piston-actuating plunger (60) includes a plunger disc (73) and at least one actuating unit (80) are arranged,
the spring-energy storage (50) includes at least one pre-stressed spring-loaded element and the bottom portion is in contacting relationship with the plunger disc (73),
at least part of the piston-actuating plunger (60) is positioned between the spring-energy storage (50) and a piston (111) of the cylinder-piston unit (100),
the housing (10) has proximate the upper region thereof at least one inverted draw hook (21), the at least one inverted draw hook (21) at least in certain areas are flexural elastic elements (28), the at least one inverted draw hook (21) has a free end proximate the bottom thereof which has at least one support surface (23) in the region of the free end, the housing (10) and the at least one inverted draw hook (21) consisting of one single piece,
the plunger disc (73) of the piston-actuating plunger (60) rests on the support surface (23) prior to actuation of the injector,
the at least one draw hook (21) and the piston-actuating plunger (60) having a contact zone therebetween in the form of a variable-speed gear pair thereby thrusting the at least one draw hook (21) radially outwards,
an actuating element (82) in releasable securing relationship with the at least one draw hook (21), the actuating element (82) has a locked position (8) to laterally secure the at least one draw hook (21), the at least one support surface (23) of the at least one draw hook (21) extending below the spring energy storage (50) in the locked position (8),
an actuating cap (59) fully enclosing the housing (10) and the spring energy storage (50) in the locked position (8) and operably engaging the actuating element (82),
the housing (10) having a substantially tubular jacket region (31) fully enclosing the spring energy store (50) in the locked position (8), the substantially tubular jacket region (31) having a cylindrical outer surface (13),
the actuating element (82) has a triggering position (9) which effects radially outwards aligned retreat of the at least one draw hook (21) into the actuating cap (59) when the piston-actuating plunger (60) is released,
the at least one inverted draw hook having a radially inwardly projecting hook element (22) proximate the substantially tubular jacket region (31), the draw hook

(21) or (21) being art of the substantially tubular jacket region (31), the draw hook (21) or draw hooks (21) including the inwardly projecting hook element (22) having a rear surface (29) having the curve of the outer cylindrical surface (13) of the substantially tubular jacket region (31) of the housing (10) for a predetermined length in the locked position (8), the radially inwardly projecting hook elements (22) in operative contact relationship with the spring-loaded piston-actuating plunger (60) proximate the plunger disc (73), in the locked position (8), the rear surface (29) of the draw hook (21) or draw hooks (21) and the remaining outer cylindrical surface (13) of the substantially tubular jacket region (31) of the housing (10) is in operative slideable relationship relative to the inner surface of the actuating element (82), whereby upon actuation of the injector, triggering of the injector may be effectuated.

2. The disposable injector according to claim 1, wherein the housing (10) is in operative slideable relationship relative to the actuating cap (59) upon actuation of the injector.

3. The disposable injector according to claim 1, wherein the support surface (23) of the at least one inverted draw hook has an inner surface of a toroid jacket part or a frustoconical surface.

4. The disposable injector according to claim 3, wherein the support surface (23) is curved convexly in one plane and at the same time is curved concavely in another plane in the case of a support surface (23) toroid-jacket-shaped in certain areas.

5. The disposable injector according to claim 1, wherein the housing (10) is hollow pot-shaped, open at the bottom thereof proximate the radially inwardly projecting hook element (22) and having an elevated floor (39) at the top of the housing (10), the housing (10) has oppositely disposed window-like openings (33) proximate the middle region thereof, the actuating element (82) is a sleeve longitudinally slidably mounted on the housing (10), the actuating cap (59) has a circumferential widened region (83) above an edge (85) of the actuating element (82) proximate the middle region of the housing (10), the at least one inverted draw hook having contact surfaces (24), the at least one inverted draw hook by the contact surfaces (24) abut radially the sleeve actuating element (82) proximate the edge (85), in the locked position (8).

6. The disposable injector according to claim 1, wherein the actuating element (82) further comprises a pivotable release lever (86) which includes a latching tab (87), the housing (10) has a recess (27), the latching tab (87) in releasable secure engagement in the recess (27) with the housing (10), in the locked position (8).

7. The disposable injector according to claim 5, further comprising a tear-off banderole (90) removably fastened to the housing (10) and the actuating element (82) in the locked position (8), in combination with the housing (10) and the tear-off banderole (90) fastened thereon the actuating element (82) forms an actuating unit (80).

8. The disposable injector according to claim 5, wherein the at least one inverted draw hook has a fixed end proximate the floor (39) and a narrow, at least U-shaped gap surrounds each of the at least one inverted draw hook (21) proximate the sides and the bottom of each of the at least one inverted draw hook (21).

9. The disposable injector according to claim 8, wherein the at least one inverted draw hook has the wall thickness of the walls of the remaining portion of the housing (10) for a predetermined length.

10. The disposable injector according to claim 8, wherein the actuating element (82) has a return flank (84) proximate the upper end thereof, the return flank (84) has an inner edge (85), the widened region (83) of the actuating cap (59) positioned immediately above the return flank (84) in the locked position (8), the at least one inverted draw hook (21) proximate the hook element (22) abut radially the actuating element (82) proximate the edge (85) in the locked position (8).

11. The disposable injector according to claim 1, wherein the housing (10) further includes a fixing region (41) under the substantially tubular jacket region (31), the cylinder-piston unit (100) includes a cylinder (101), the cylinder (101) includes bayonet catches (44), the fixing region (41) having on its inner walls at least two angular channels (42), the bayonet catches (44) of the cylinder (101) engage the angular channels (42) in an operative position.

12. The disposable injector according to claim 11, wherein the cylinder (101) has a cylindrical bore, the piston (111) is operatively positioned within the cylindrical bore of the cylinder (101), a protective cap (120) is removably affixed to the cylinder 101 in sealing relationship therewith in the locked position (8).

* * * * *